United States Patent [19]
Hitchcock et al.

[11] Patent Number: 5,933,335
[45] Date of Patent: Aug. 3, 1999

[54] COMPACT SOLID STATE KLYSTRON POWER SUPPLY

[75] Inventors: Roger N. Hitchcock, San Leandro; Michael J. Marziale, El Sobrante; Lance W. Thompson, San Leandro, all of Calif.

[73] Assignee: Siemens Medical Systems, Inc., Iselin, N.J.

[21] Appl. No.: 09/007,574

[22] Filed: Jan. 15, 1998

Related U.S. Application Data

[63] Continuation-in-part of application No. 08/704,054, Aug. 28, 1996.

[51] Int. Cl.⁶ .................................................. H02M 3/335
[52] U.S. Cl. ............................ 363/25; 363/133; 315/408
[58] Field of Search ................................. 363/21, 25, 26, 363/89, 133, 134; 307/110; 219/715, 716, 761; 315/387, 408

[56] References Cited

U.S. PATENT DOCUMENTS

| | | | |
|---|---|---|---|
| 4,302,651 | 11/1981 | Wills | 323/323 |
| 4,835,353 | 5/1989 | Smith et al. | 363/132 |
| 5,045,658 | 9/1991 | Smith | 219/516 |
| 5,083,093 | 1/1992 | Adler et al. | 328/65 |
| 5,181,160 | 1/1993 | Okamoto et al. | 363/97 |
| 5,321,235 | 6/1994 | Makino et al. | 363/21 |
| 5,483,122 | 1/1996 | Derbenev et al. | 315/500 |
| 5,764,002 | 6/1998 | Jennings | 315/408 |

*Primary Examiner*—Robert E. Nappi
*Assistant Examiner*—Derek J. Jardieu

[57] ABSTRACT

A line type modulator for modulating an RF power device in a medical linear accelerator is described. The modulator employs a low voltage DC power source and a flyback transformer. Current sensing circuitry senses current in the primary winding of the flyback transformer and generates a current sense signal indicative thereof. A solid-state switching stage is coupled between the DC power source and the flyback transformer which electrically connects and disconnects the DC power source and the primary winding in response to a control signal. Control circuitry coupled to the current sensing circuitry and the switching stage generates the control signal in response to the current sense signal. The anode of a charge diode assembly is coupled to the secondary winding of the flyback transformer. A delay element is coupled to the cathode of the charge diode assembly. A pulse forming network is coupled to the delay element and generates an energy pulse. A solid-state switch assembly is also coupled to the cathode of the charge diode assembly and discharges energy stored in the pulse forming network via the delay element in response to a trigger signal. A pulse transformer coupled to the pulse forming network delivers the energy pulse to the RF power device.

21 Claims, 10 Drawing Sheets

Note: Waveforms not to scale.

COMPACT SOLID STATE KLYSTRON POWER SUPPLY

CROSS-REFERENCE TO RELATED APPLICATION

The present application is a continuation-in-part of U.S. patent application Ser. No. 08/704,054 for COMPACT SOLID STATE KLYSTRON POWER SUPPLY filed on Aug. 28, 1996, the entire specification of which is incorporated herein by reference for all purposes.

BACKGROUND OF THE INVENTION

The present invention relates to power supplies, and more particularly, to a compact power supply for use in powering linear accelerators, and the like. Still more particularly, the present invention relates to a solid-state line type modulator for modulating a klystron in a medical linear accelerator.

Radiation-emitting devices are generally known and used, for instance as radiation therapy devices for the treatment of patients. A radiation therapy device generally comprises a gantry which can be swiveled around a horizontal axis of rotation in the course of a therapeutic treatment. A linear accelerator is located in the gantry for generating a high energy radiation beam for therapy. This high energy radiation beam can be an electron or photon (X-ray) beam. During treatment, this radiation beam is trained on one zone of a patient lying in the isocenter of the gantry rotation.

In this arrangement, radiation is generated by applying an electron beam to a target to generate x-rays. The electron beam is typically generated in a linear accelerator that is powered by a klystron based power supply having a power output in the 10 to 30 kW range. FIG. 1 is a block diagram of a medical linear accelerator showing major components and auxiliary systems. Power supply 10 provides D.C. power to modulator 12. Modulator 12 includes a pulse forming network and a switch tube known as hydrogen thyratron. A thyratron is a low pressure gas device with a thermionic cathode. Over time, the cathode depletes itself. Thus, a thyratron has an inherent wear out mechanism. The high voltage pulses from modulator 12 are flat-topped D.C. pulses of a few microseconds in duration. These pulses are delivered to magnetron or klystron 14 and simultaneously to electron gun 16. Pulsed microwaves produced in magnetron or klystron 14 are injected into accelerator tube 20 via waveguide system 22. At the proper instant, electrons, which are produced by electron gun 16, are also pulse injected into accelerator tube 20. High energy electrons emerge from accelerator tube 20 in the form of a beam of approximately 3 mm in diameter. These electrons can be fed to treatment head 24 as a straight beam or to treatment head 26 as a bent beam. If the electrons are sent to treatment head 26, the electrons are bent by, for example, bending magnet 28 through a suitable angle (e.g., 270 degrees) between accelerator tube 20 and the target.

Prior art power supplies for linear accelerators are large, heavy devices that significantly increase the cost and size of the medical treatment system. One typical prior art system utilizes a high voltage transformer/rectifier system to generate a 21 kV DC power source from a conventional three-phase 208 V power source. The high voltage DC source is then used to generate a 15 kV pulse that is converted to the required 150 kV pulse via a high voltage pulse transformer. The high voltage transformer/rectifier assembly typically weighs 500 lbs. and occupies 8 cubic feet. As a result, the power supply must be housed in a separate cabinet from the linear accelerator. In addition to increasing the floor space needed to house the accelerator system, this additional cabinet requires special power transmission lines to couple the klystron output to the linear accelerator which further increases the cost and complexity of the system. Finally, the sheer weight of the system increases the cost of shipping.

The manner in which the present invention gains its advantages over the prior art may be more easily understood with reference to FIG. 2 which is a block diagram of a typical power system 50 for powering a klystron. Power system 50 converts 208 volt, 3 phase power to 15 kV, 1200 amp. pulses of approximately 5:s duration. These pulses are stepped up to 150 kV by pulse transformer 85 whose output drives the klystron. The 15 kV pulses are generated by a pulse generating circuit that is powered by a 21 kV D.C. source. The 21 kV D.C. source is typically a high voltage transformer and rectifier assembly 60. As noted above this D.C. power supply typically occupies 8 cubic feet and weighs approximately 500 lbs.

The high voltage pulse generating circuit typically consists of an inductor 72 which resonantly charges a pulse forming network 76. The final pulse amplitude that is applied to the klystron is adjusted by controlling the amount of time a high voltage charge switch 71 is closed. The system measures the current flowing through a resistor 73 and the voltage at the pulse forming network 76 to determine the timing of the switch opening. The connection to the pulse forming network has been omitted from the drawing. A controller 74 utilizes the current and voltage measurements to control the switch closure duration. It should be noted that the range of adjustment in the final pulse amplitude that can be obtained with the inductor design shown in FIG. 2 is limited because only a portion of the energy of the final pulse is stored in inductor 72. It should also be noted that the conversion of the 208 volt power to a 21 kV D.C. source requires a substantial number of high voltage components that must operate at high power levels which require high voltage insulation and pose safety problems. Two more detailed examples of conventional high voltage pulse generating circuits are shown in FIGS. 3 and 4.

Referring to FIG. 3, a schematic of a high voltage power system 500 employing a command charge modulator. A brute force HVDC power supply 502 provides filtered 21 kVDC to the plate of a tetrode 504. In quiescence, tetrode 504 is biased off, thyratron 506 is nonconducting, PFN 508 has no charge, and the cathode of klystron 510 is at ground potential. Upon application of a gate pulse to the control grid of tetrode 504, tetrode 504 switches on. Tetrode 504 is operated as a switch, so tetrode driver 512 is designed to drive tetrode 504 into saturation. PFN 508 starts to resonantly charge through charge inductor 514. The energy in PFN 508 is monitored via voltage divider 516, and the energy in charge inductor 514 is monitored via charge current sense resistor 516. A regulator circuit (not shown) sums the energy of charge inductor 514 and PFN 508 and commands tetrode 504 to switch off when the sum of the energies reaches a desired value. Since current is flowing in charge inductor 514 when tetrode 504 opens, freewheeling diode 518 is needed to provide a path for the inductor current to continue to flow until the inductor energy reaches zero as PFN 508 accumulates the remaining inductor energy.

The impedance of PFN 508 is designed to be slightly higher than the reflected impedance of klystron 510. This causes PFN 508 (which acts like a transmission line) to reflect a negative pulse back to thyratron 506, which is needed to assist in shutting off thyratron 506 at the end of the discharge cycle. Inverse diode-resistor assembly 520 maintains this inverse voltage long enough to ensure full recovery of thyratron 506.

Core bias power supply 522 is used to help reset the core of pulse transformer 524, and choke 526 is placed in series with power supply 522 to oppose pulse current entering the supply. A backswing clipper 528 absorbs energy remaining in the core of pulse transformer 524 due to magnetizing current, thereby preventing klystron 510 from being reverse biased, and reducing the size required of the core, which would otherwise have to dissipate this energy as core loss.

The disadvantages of this type of modulator include its large bulk and weight, the massive HVDC power supply, the need for a tetrode floating at high voltage with accompanying floating control circuitry, the need for a HV freewheeling diode, and rather complex regulating circuitry. An advantage this system has over the DeQ system described below is that it can produce pulses at a very low repetition rate. It produces a pulse for the klystron when it is commanded to, and all pulses are the same in amplitude, no matter how low the repetition rate. This system also has the advantage of a wide range of regulation, limited by the switching time of the tetrode.

Referring to FIG. 4, a schematic of another high voltage power system 550 employing a DeQ regulated line type modulator is shown. As can be easily seen, this modulator is very similar to command charge system 500 described above with reference to FIG. 3, but tetrode 504 and its support circuitry have been replaced with a DeQ thyratron 552 and series resistor 554 in shunt with charge inductor 514. Modulator elements having the same or similar function as corresponding elements described with reference to FIG. 3 will be similarly numbered.

In quiescence, PFN 508 has charged to the potential of HVDC power supply 502 through charge inductor 514, DeQ thyratron 552 is off, the main switch thyratron 506 is off, and no current flows in klystron 510. Upon application of the thyratron trigger, PFN 508 is discharged into the primary of klystron pulse transformer 524. PFN 508, having been discharged quickly, will resonantly charge to about twice the HVDC power supply potential. This voltage would be too high. However, the PFN energy is monitored via voltage divider 556, and a regulator circuit (not shown) compares the PFN energy with a reference value and switches DeQ thyratron 552 on when the desired energy has been reached. DeQ thyratron 552 kills the Q of charge inductor 514, stopping the resonant charging of PFN 508. Main switch thyratron 506 discharges PFN 508 into pulse transformer 524, causing the PFN-inductor to resonantly charge again as the cycle continues.

The disadvantages of this type of modulator include the HVDC power supply, the complexity of a floating DeQ thyratron assembly, and poor regulation at low PRF, due to the fact that the PFN charge bleeds off through the voltage divider during the interpulse period. The regulation range is limited by the inductance of the charging choke. The charging choke must be linear or nearly linear to prevent saturation and circuit instabilities resulting from short duration saturation. As linearity increases, so does the required size, weight, and cost of the choke. Also, inadvertent triggering of the main thyratron during the charge cycle will cause the volt-second product of the charge inductor to be exceeded. The heavily saturated inductor will then allow the HVDC power supply to short circuit into the main thyratron, possibly damaging charge diode 517, the HVDC power supply, and the thyratron unless appropriate fusing is provided.

It is therefore desirable to provide a line type modulator for modulating RF power devices which does not suffer from the foregoing disadvantages.

SUMMARY OF THE INVENTION

Broadly, it is the object of the present invention to provide an improved high voltage power system for powering klystrons and the like. It is a further object of the present invention to provide a high voltage power system that requires less space than prior art high voltage power systems. It is a still further object of the present invention to provide a high voltage power system that is significantly lighter than prior art power supply systems.

To achieve these objectives, the present invention provides a line type modulator having discontinuous mode flyback topology. Notably, according to the present invention, no HVDC power supply is used. Instead, power is derived directly from a low power AC line using a relatively small low voltage 3-phase bridge rectifier. No floating charge inductor is required. In its place is the secondary of a flyback transformer. No floating HV thyratrons or tetrodes are required to provide regulation. Instead two insulated gate bipolar transistors (IGBTs) floating at a low voltage are used. In addition, according to the present invention, a thyratron is not used as the main PFN discharge switch. Instead, a solid state switch assembly consisting of a stack of thyristors, i.e., silicon controlled rectifiers (SCRs) is employed. These devices, besides having no built in wearout mechanisms, do not require a negative voltage to assure turnoff, thereby obviating the need for a large power resistor in the inverse diode assembly.

Thus, the present invention provides a line type modulator for modulating an RF power device in a medical linear accelerator. The modulator employs a low voltage DC power source and a flyback transformer. Current sensing circuitry senses current in the primary winding of the flyback transformer and generates a current sense signal indicative thereof. A solid-state switching stage is coupled between the DC power source and the flyback transformer which electrically connects and disconnects the DC power source and the primary winding in response to a control signal. Control circuitry coupled to the current sensing circuitry and the switching stage generates the control signal in response to the current sense signal. The anode of a charge diode assembly is coupled to the secondary winding of the flyback transformer. A delay element is coupled to the cathode of the charge diode assembly. A pulse forming network is coupled to the delay element and generates an energy pulse. A solid-state switch assembly is also coupled to the cathode of the charge diode assembly and discharges energy stored in the pulse forming network via the delay element in response to a trigger signal. A pulse transformer coupled to the pulse forming network delivers the energy pulse to the RF power device.

A further understanding of the nature and advantages of the present invention may be realized by reference to the remaining portions of the specification and the drawings.

DESCRIPTION OF SPECIFIC EMBODIMENTS

Figure 1:
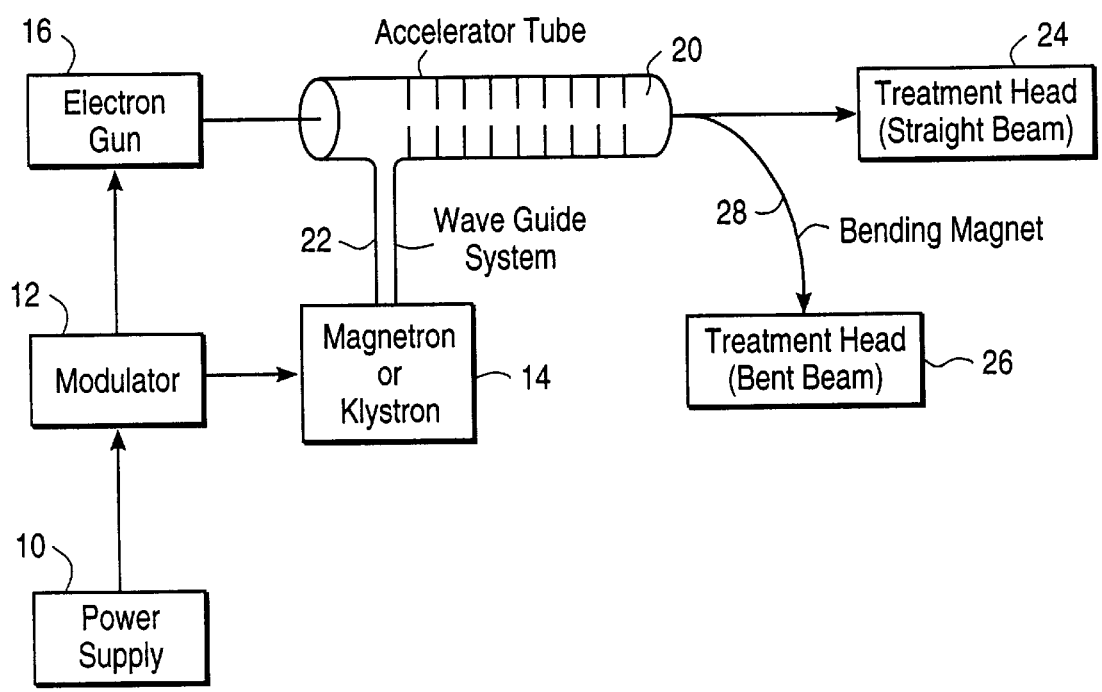
FIG. 1 is a block diagram of a medical linear accelerator showing major components and auxiliary systems.
Figure 2:
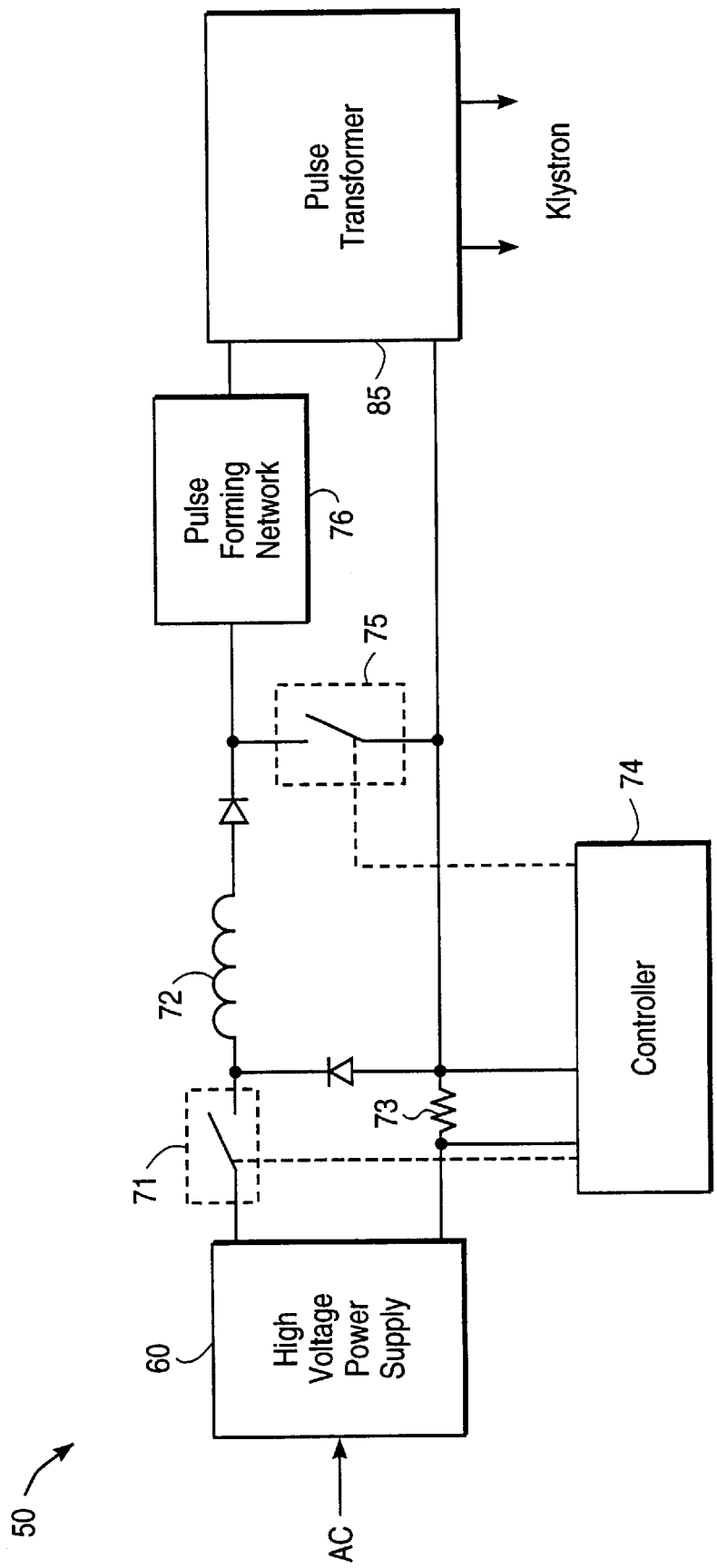
FIG. 2 is a block diagram of a typical prior art power supply system for operating a klystron for driving a linear accelerator.
Figure 4:
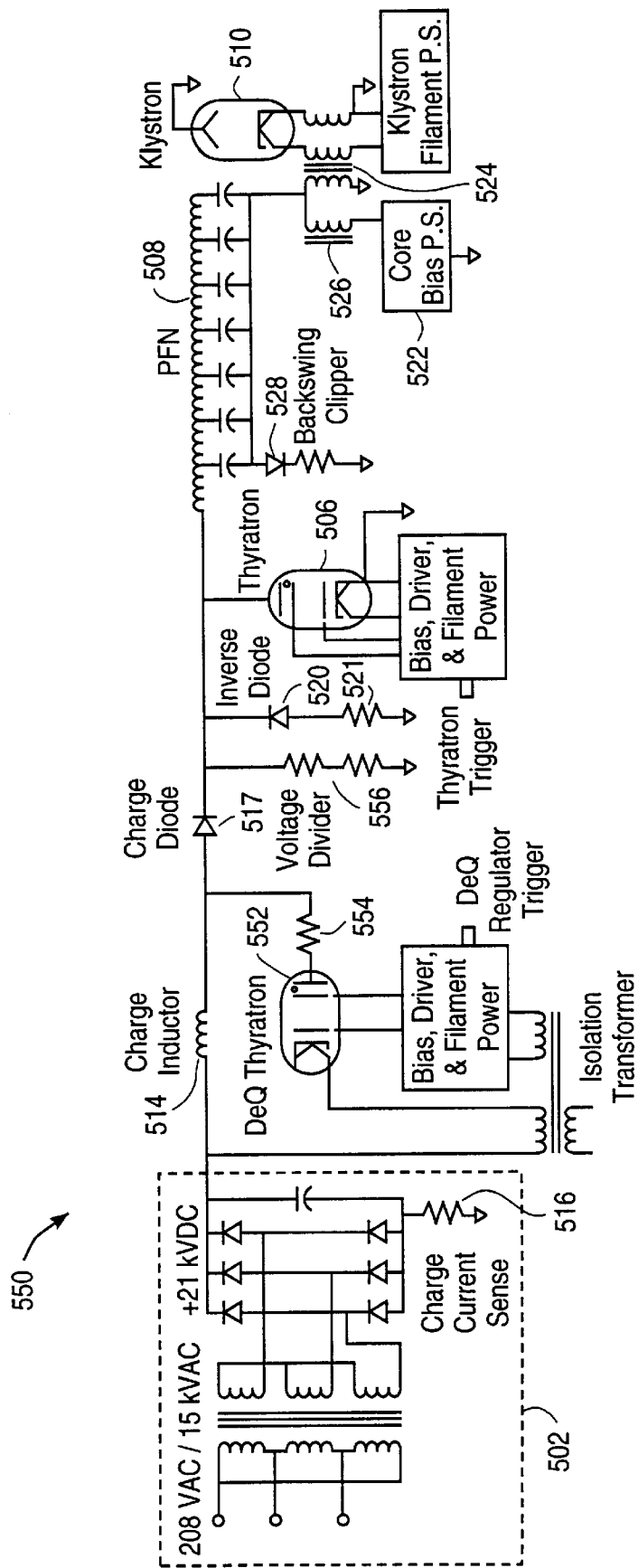
FIG. 4 is a schematic showing a DeQ regulated line type modulator.
Figure 5:
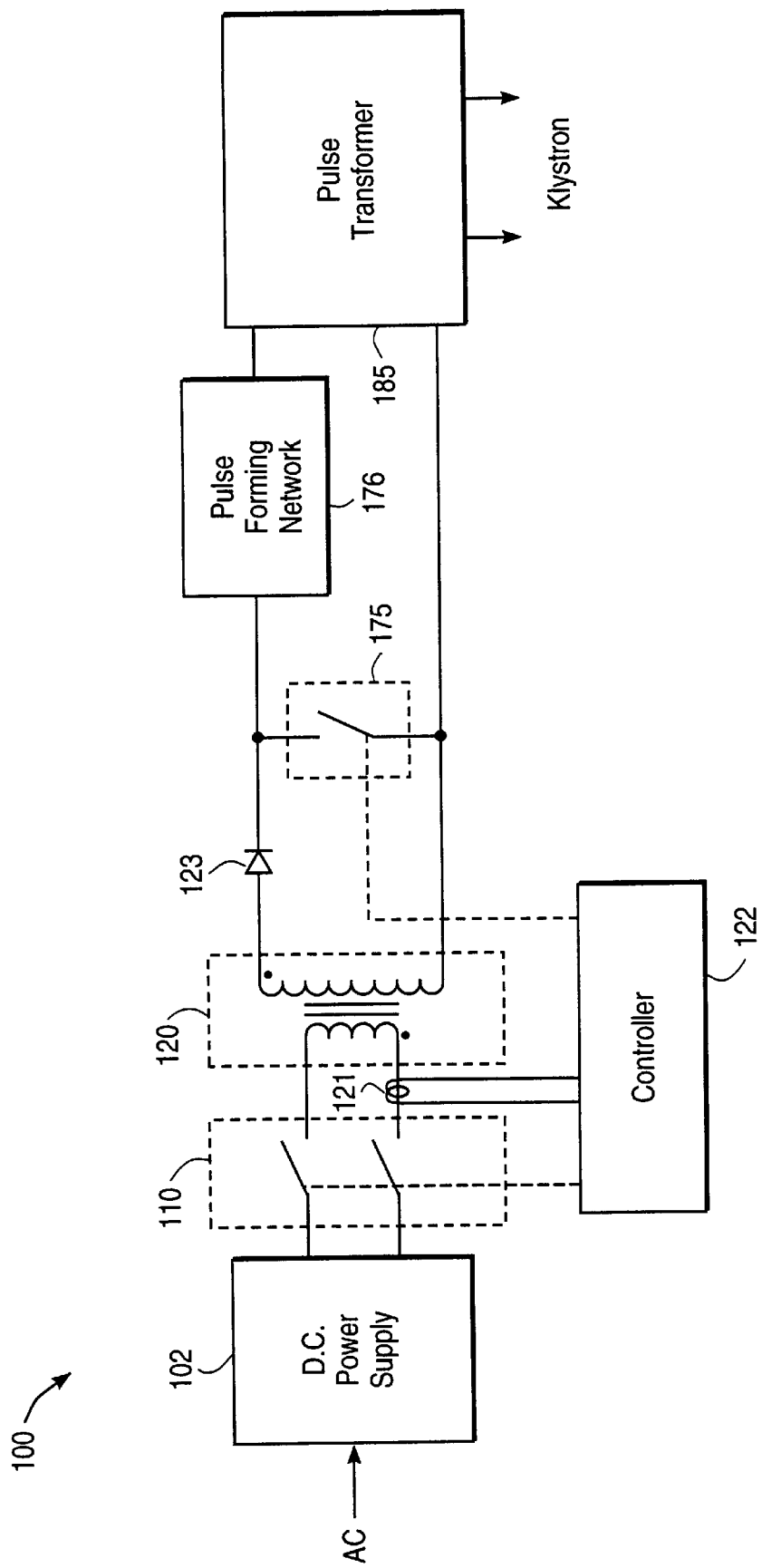
FIG. 5 is a block diagram of one embodiment of a high voltage power system according to the present invention.

FIG. 5 is a block diagram of a high voltage power system 100 according to the present invention. The present invention utilizes a flyback transformer 120 to power pulse forming network 176. Flyback transformer 120 is powered from a 300 volt D.C. power supply 102. This is a significant reduction from the 21 kV D.C. power supply used in the prior art. A solid state switch 110 is used to control the output voltage from flyback transformer 120. A controller 122 senses the current flowing in the primary of flyback transformer 120, as shown at 121. When the current reaches the desired level, switch 110 is opened, and the energy stored in flyback transformer 120 is transferred to pulse forming network 176 via charge diode 123. After pulse forming network 176 is charged, high voltage switch 175 is closed to discharge pulse forming network 176 thereby transferring the energy stored in pulse forming network 176 to the primary of pulse transformer 185. The operation of pulse forming network 176 and pulse transformer 185 are substantially the same as described above with respect to the typical klystron power system shown in FIGS. 2–4.

It should be noted that flyback transformer 120 stores 100 percent of the energy that is later transferred to the klystron pulse. Hence, the present invention provides a greater range of control over the output pulse amplitude sent to the klystron. The control of the pulse amplitude is also simplified by the present invention. The pulse amplitude is controlled by opening switch 110 in response to a predetermined current being sensed in the primary of flyback transformer 120. Switch 110 operates at only 300 volts, in contrast to switch 71 shown in FIG. 2 which must operate at 21 kV. Hence, a significant savings in cost is achieved in addition to improved reliability and safety.

Further, since flyback transformer 120 is driven by a low voltage power source, the problems associated with the high voltage power supply are avoided. Power supply 102 requires approximately ¼ cubic feet of space and weighs only about 5 lbs (an 800 lb weight reduction). In addition, the lower operating voltage provides increased safety and reliability.

The basic flyback transformer design shown in FIG. 5 has been used in low power systems for some time. However, practical realizations of such a power supply for high power output have not been heretofore available. In particular, a practical implementation of switch 110 has been lacking. The vacuum tetrode used in the prior art contains an inherent wear out mechanism (the cathode), thus a solid state design is more desirable. In the present invention, switch 110 is implemented as a pair of insulated gate bipolar transistors (IGBTs).

Figure 6:
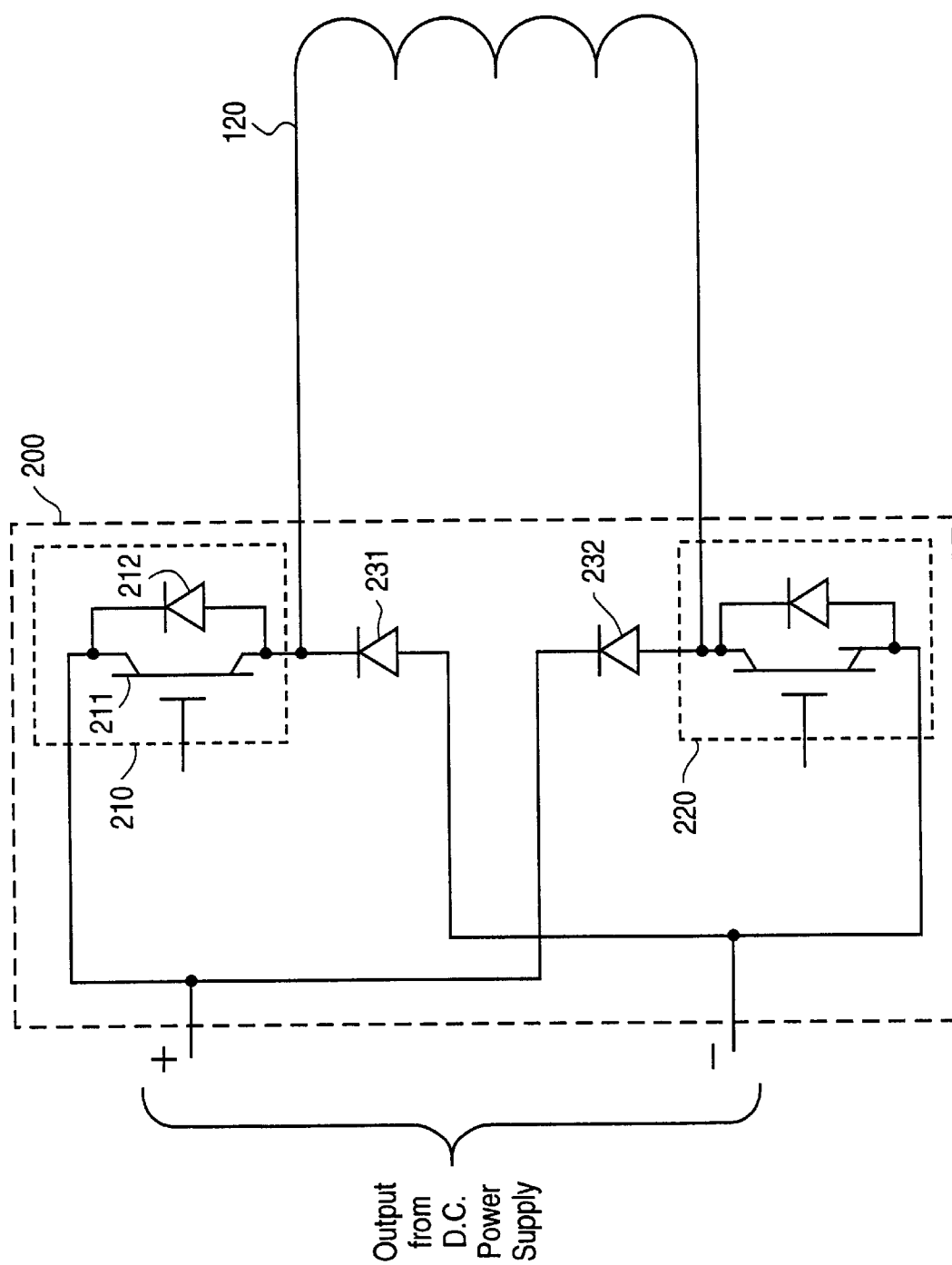
FIG. 6 is a schematic diagram of a power switch according to the present invention.

FIG. 6 is a schematic drawing of a power switch 200 according to the present invention. Power switch 200 utilizes two switching circuits shown at 210 and 220. Each switching circuit includes an IGBT 211 and a shunt diode 212. Switching circuits 210 and 220 are commercially available. Switching circuits 210 and 220 connect the D.C. power supply to the primary of flyback transformer 120. When switching circuits 210 and 220 disconnect the primary of flyback transformer 120 a reverse potential is generated across the primary winding. Shorting diodes 231 and 232 prevent this potential from damaging switching circuits 210 and 220, respectively. Shorting diodes 231 and 232 redirect this energy to the D.C. power supply where it is stored in the filter capacitors therein. As a result, the power is recovered for use in the next pulse.

Figure 7:
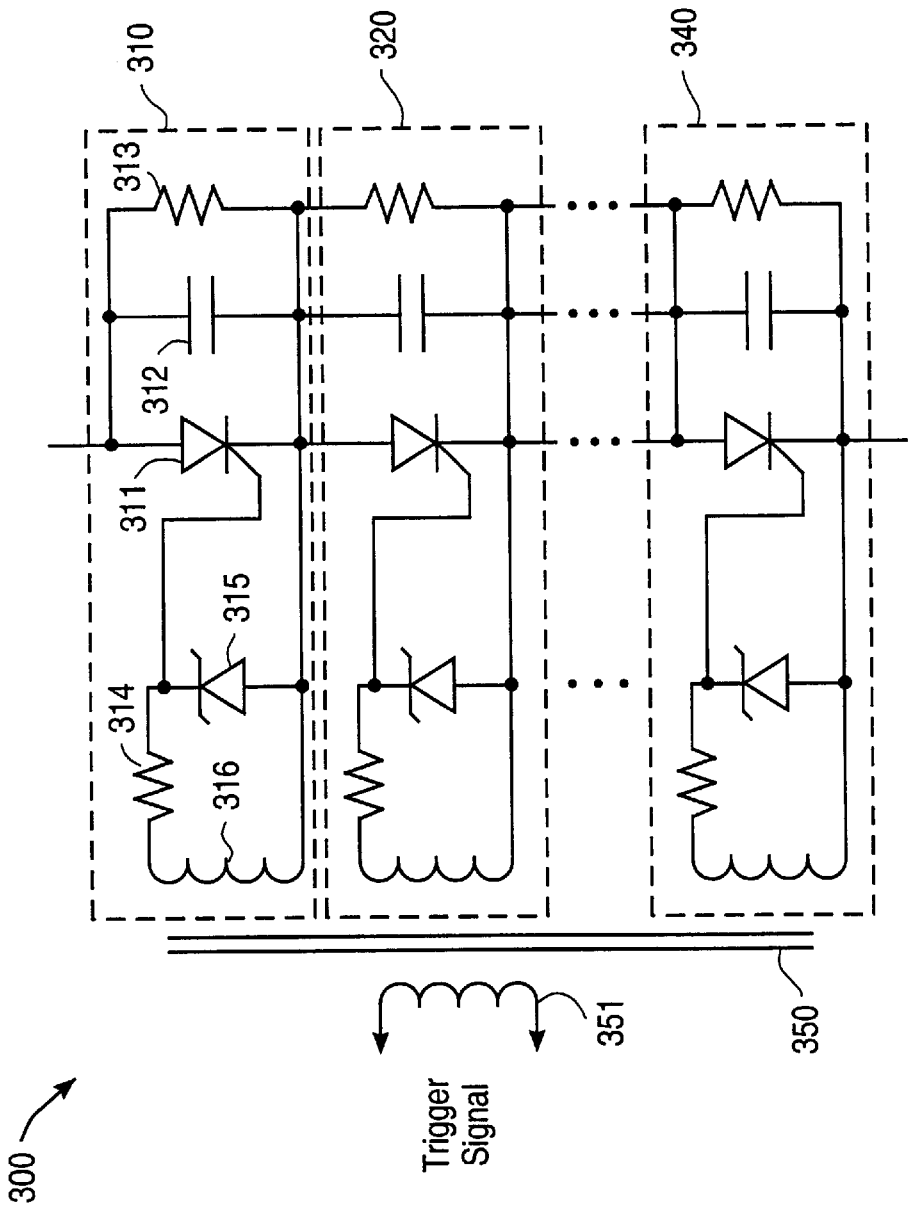
FIG. 7 is a schematic diagram of a high voltage switch according to the present invention.

According to a specific embodiment of the present invention, high voltage switch 175 (see FIG. 5) is implemented as a high voltage semiconductor controlled rectifier (SCR) stack (i.e., a number of SCRs in series). In prior art systems, the analogous switch is typically implemented with a gas thyratron which is less reliable and more costly than the SCR stack used in the present invention. A specific embodiment of a high voltage switch according to the present invention is shown in FIG. 7 at 300. Switch 300 is constructed from a number of SCR stages connected in series. The first, second, and last stages are shown at 310, 320 and 340, respectively. Each stage includes an SCR in parallel with a resistor and a capacitor, the resistor and capacitor being connected between the anode and cathode of the SCR. For example, stage 310 includes SCR 311, capacitor 312 and resistor 313. The capacitors and resistors are also connected in series to form a voltage divider network. The voltage divider assures that the same voltage is applied across each of the SCRs when the SCRs are not conducting. In the absence of the voltage divider, differences in the impedances of the SCRs in the non-conducting state can lead to different potentials being realized across each SCR when the SCR stack is not conducting. This can result in one of the SCRs being subjected to a potential difference in excess of its breakdown voltage.

The stack is triggered by coupling a signal through the inductor 316 in each stage. These inductors are the secondary stage of a pulse transformer 350, the signal being applied to the primary 351 of pulse transformer 350. Each stage includes a resistor and zener diode that assures that the trigger voltage between the gate and cathode of the SCR in each stage are the same for each stage. The resistor and zener diode in the first stage are shown at 314 and 315, respectively.

Figure 8:
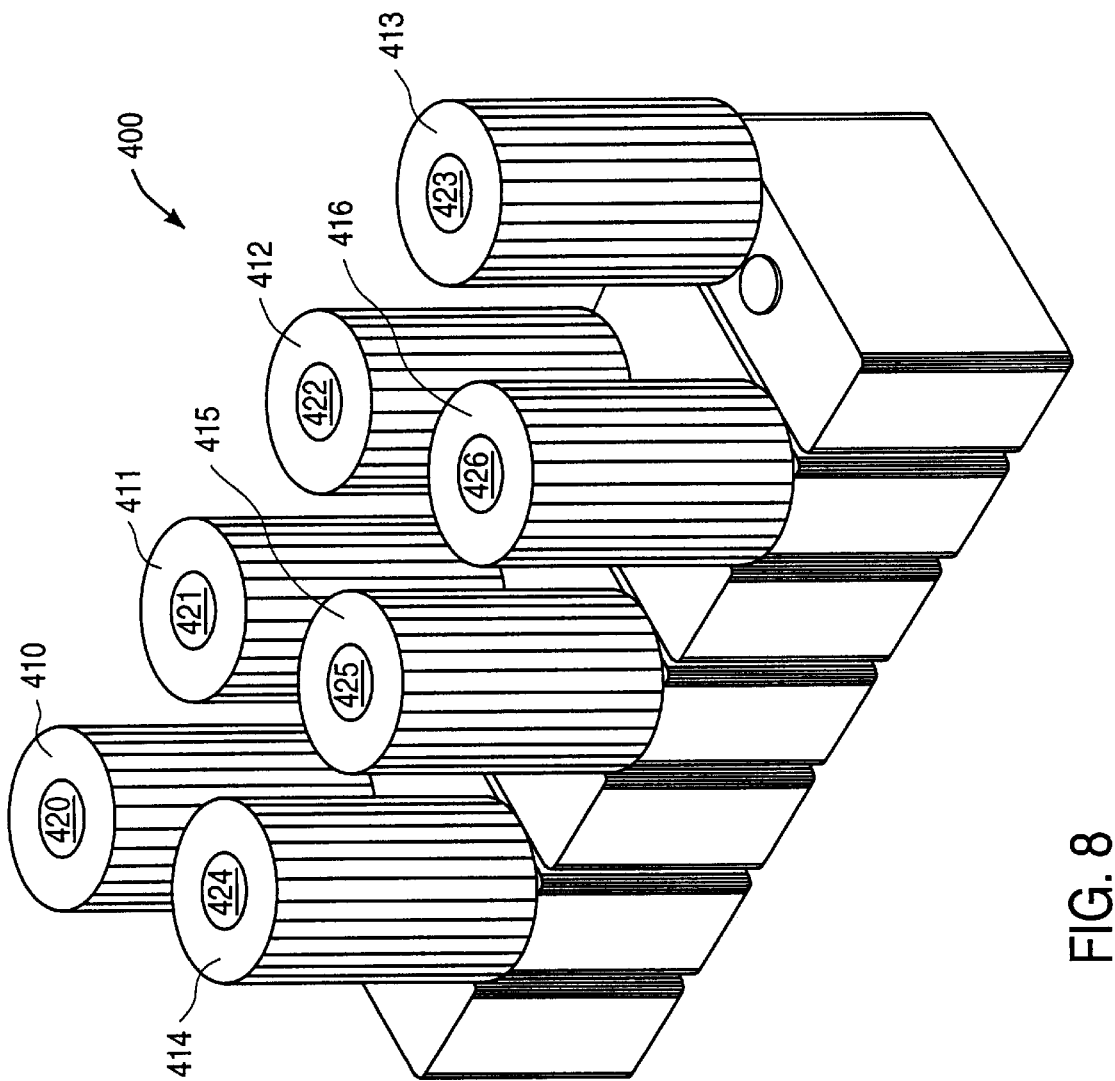
FIG. 8 is a block diagram of the pulse forming network in a specific embodiment.

In the pulse forming network, the inductor design is improved. In particular, the inductance is made to be adjustable while the system is running. FIG. 8 is a block diagram of the pulse forming network according to a specific embodiment of the invention. Pulse forming network 400 includes inductors 410–416. Usually, in a pulse forming network, a clip is placed on the inductors and the system must be shut down to manually change the inductance. The inductance is changed to fine tune the wave shape provided by the pulse forming network. This shutting down of the system and reviewing the wave shape is typically done repeatedly until the desired wave shape is obtained. A specially trained individual requires approximately 1 hour to fine tune the wave shape. In contrast, the present design uses aluminum slugs 420–426 which are placed inside inductors 410–416. Each of aluminum slugs 420–426 can be moved up and down while the system is running to vary the inductance and fine tune the wave shape. Aluminum slugs 420–426 can be moved either manually or automatically. With this improved design, fine tuning takes approximately 3 minutes.

Figure 9:
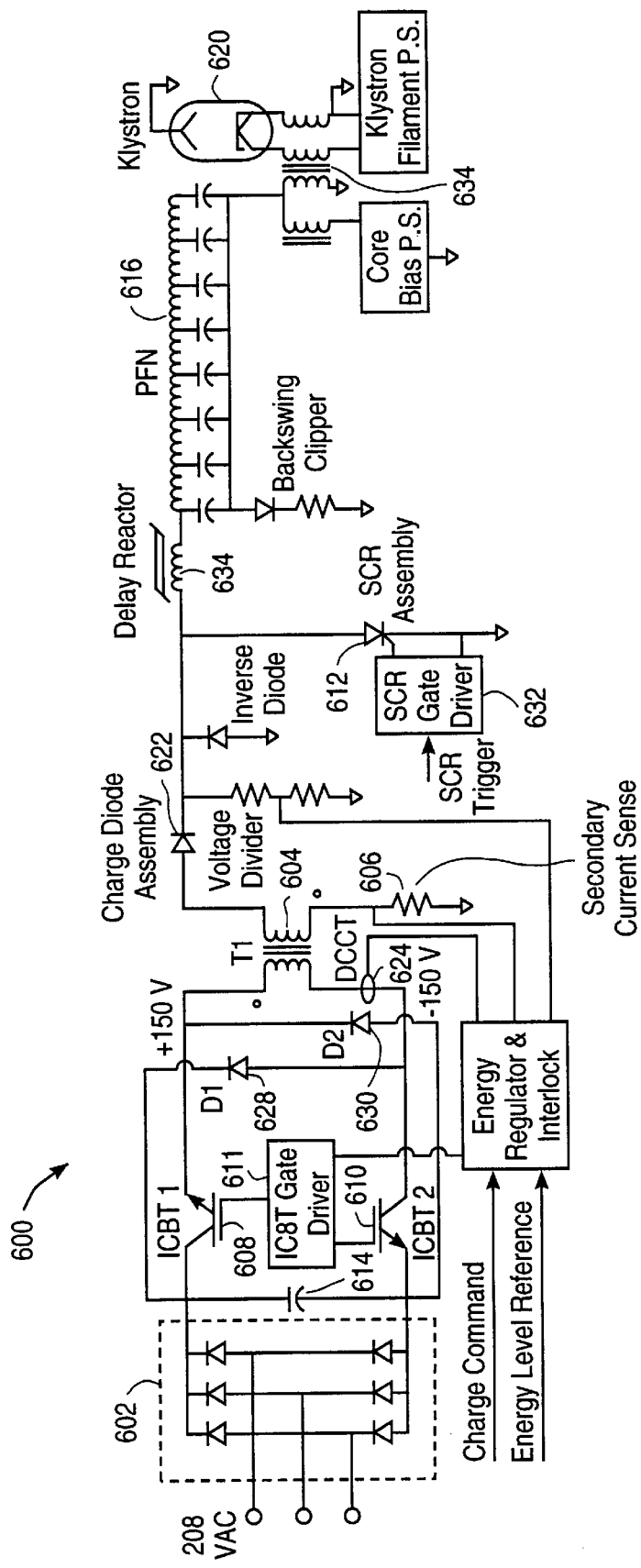
FIG. 9 is a schematic diagram of a high voltage power system according to a specific embodiment.

FIG. 9 is a schematic of a specific embodiment of a high voltage power system 600 designed according to the discontinuous mode flyback topology of the present invention. The modulator shown is a line type which is quite different from the topologies discussed with reference to FIGS. 2–4. Note that no HVDC power supply is used. Instead, power is derived directly from a 208 VAC line. A low voltage 3-phase bridge rectifier 602 is used, which is only 7 cubic inches in volume. No floating charge inductor is required. In its place is the secondary of a flyback transformer 604 which has one side tied to ground through a 1 ohm current sense resistor 606. No floating HV thyratrons or tetrodes are required to provide regulation. In their place are two insulated gate bipolar transistors (IGBTs) 608 and 610, which are floating at a low voltage (+150 V, and −150 V). No thyratron is used as the main PFN discharge switch. Instead, a solid state switch assembly 612 consisting of a stack of thyristors, i.e., silicon controlled rectifiers (SCRs) is employed. These devices, besides having no built in wearout mechanisms, do not require a negative voltage to assure turnoff, thereby obviating the need for a large power resistor in the inverse diode assembly.

The operation of the line type modulator of FIG. 9 will now be described with reference to the waveforms of FIGS. 10a–10e. During quiescence, the DC power supply energy storage capacitor 614 is charged to about 300 VDC. IGBTs 608 and 610 are switched off. No current flows in flyback transformer 604. Note that although the term "transformer" is used here, this device operates more as an energy transfer coupled inductor. That is, a transformer typically transforms current and voltage from a primary to a secondary, or multiple secondaries, in a continuous fashion. This device stores energy, and operates discontinuously. PFN 616 has no charge. Thyristor switch 612 is off. Klystron 620 has no potential between its anode and cathode.

Figure 10A:
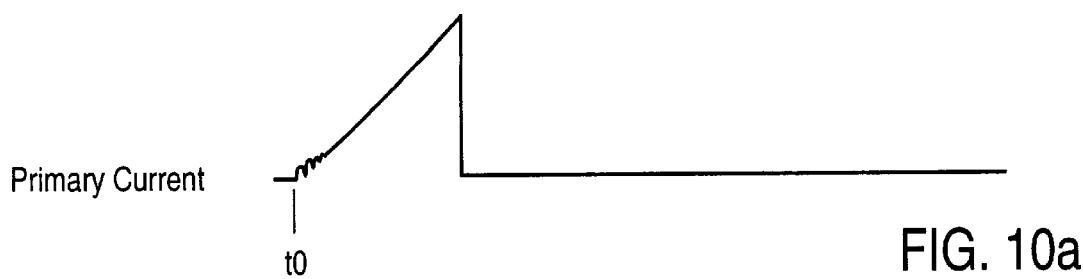
FIGS. 10a–10e depict waveforms which can be monitored at various locations during the operation of the high voltage power system of FIG. 9.
Figure 10B:
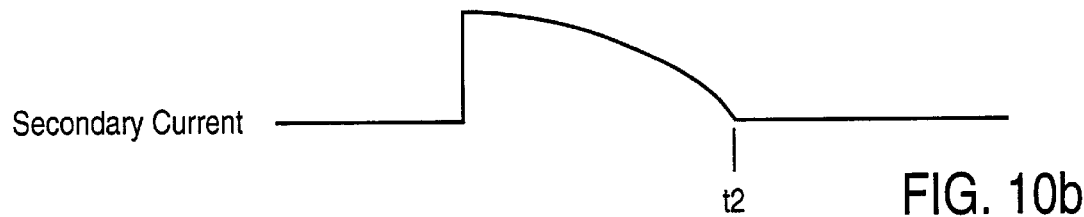
Figure 10C:
Figure 10D:
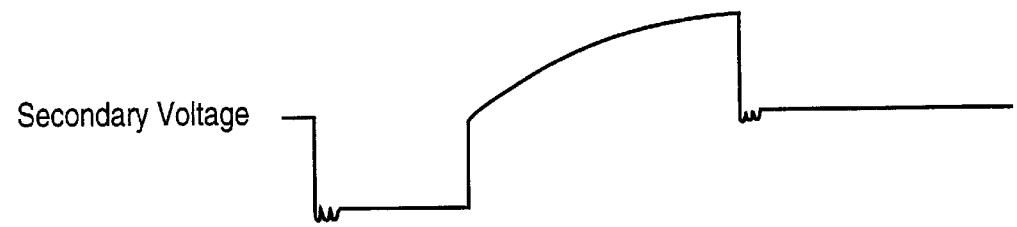
Figure 10E:
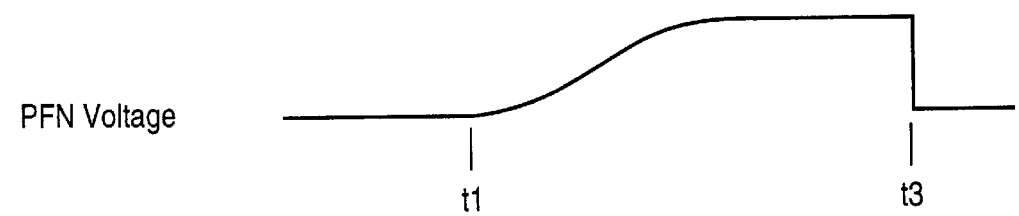

At $t_0$, IGBT switches 608 and 610 are commanded to close via IGBT gate driver circuitry 611. This causes current to flow in the primary of flyback transformer 604 as a linear ramp, whose slope, di/dt, is determined by the primary inductance and the DC power supply potential per the equation: di/dt=V/L (FIG. 10a). Note that secondary current (FIG. 10b) does not flow because the transformer windings are oppositely wound. When the voltage at the top of the primary winding is positive (FIG. 10c), the voltage at the top of the secondary becomes negative (FIG. 10d), so charge diode 622 is reverse biased. While the primary current is flowing, energy is being stored in the gap of the core of flyback transformer 604. The current ramp is monitored by DC current transformer (DCCT) 624. This signal is sent to energy regulator circuit 626 which squares the signal, thus producing a signal proportional to stored energy per the equation: $W=\frac{1}{2}LI^2$. This energy term is compared to a reference DC level and, when the DC level is reached, energy regulator 626 commands IGBTs 608 and 610 to open via IGBT gate driver circuitry 611. This occurs at $t_1$ in FIG. 10. According to one embodiment, isolation is provided between energy regulator circuitry 626 and IGBT gate driver circuitry by means of optical coupling.

Upon opening of IGBTs 608 and 610, current stops flowing from the DC power supply. Primary current decays quickly, but not instantaneously due to the leakage inductance of the primary circuit. This leakage inductance had stored energy when the primary current was flowing, but does not couple this energy to the secondary. When the switches open, this stored energy, which by definition does not transfer to the secondary, tends to keep current flowing in the primary. Freewheeling diodes 628 and 630 provide a path for this current to flow back into the DC power supply. If these diodes were not present, a potential would build up very quickly across the primary winding until an arc occurred or the IGBTs voltage holdoff capabilities were exceeded. Diodes 628 and 630 ideally clamp this voltage to the power supply voltage plus their voltage drops, which is on the order of one volt each. The power supply and path impedances are not zero, so a short duration voltage spike exceeding the power supply voltage, but at a benign amplitude, appears across the primary (see the negative spike of the primary voltage in FIG. 10c). So this circuit acts as a nearly lossless clamp, restoring the energy stored in the leakage inductance to the DC supply, thereby improving the efficiency of the charge system, and reducing the amplitude of potentially harmful voltage transients.

An alternative to this method would be the use of a single IGBT, with any of a number of snubber and clamp circuits. Most such schemes are lossy, however, as they provide a resistive element to dissipate the stored energy. A design using only one IGBT actually turns out to be more complex and use more devices than the design of FIG. 9. Moreover, such a design requires a higher voltage IGBT, since the device would see the full DC power supply potential, whereas the design of FIG. 9 splits this voltage across two devices.

As energy from the core of flyback transformer 604 transfers to PFN 616, the voltage on PFN 616 (FIG. 10e) rises until all the stored energy, minus circuit losses, is transferred to PFN 616 ($t_2$). The PFN potential will then be equal to $[2^* (W_{primary}-W_{loss})/C]^{1/2}$.

At a time $t_3$ determined by the desired pulse repetition period (PRP), SCR assembly 612 is commanded to switch on via SCR Gate Driver 632. Delay reactor 634 has a volt-second product which inhibits the transfer of PFN energy to SCR assembly 612 until the gate-cathode junctions of the SCRs in the stack are enhanced. That is, the SCRs used in this application are rather slow, and require a few microseconds to fully turn on. If delay reactor 634 was not used, the SCR impedance, which drops very soon after the gate drive pulse appears, would be low enough to allow enough energy from PFN 616 to be transferred through the switch to damage it. The current would pass through a small portion of the cathode, causing a hot spot which would burn through the device. Delay reactor 634 holds off the PFN voltage until SCR assembly 612 saturates, at which time PFN 616 quickly dumps through the adequately enhanced SCRs. The advantage of using these slow, but very robust SCRs in concert with the delay reactor is very low cost in comparison to the high cost of fast SCRs. Currently, the cost factor is about three.

Figure 3:
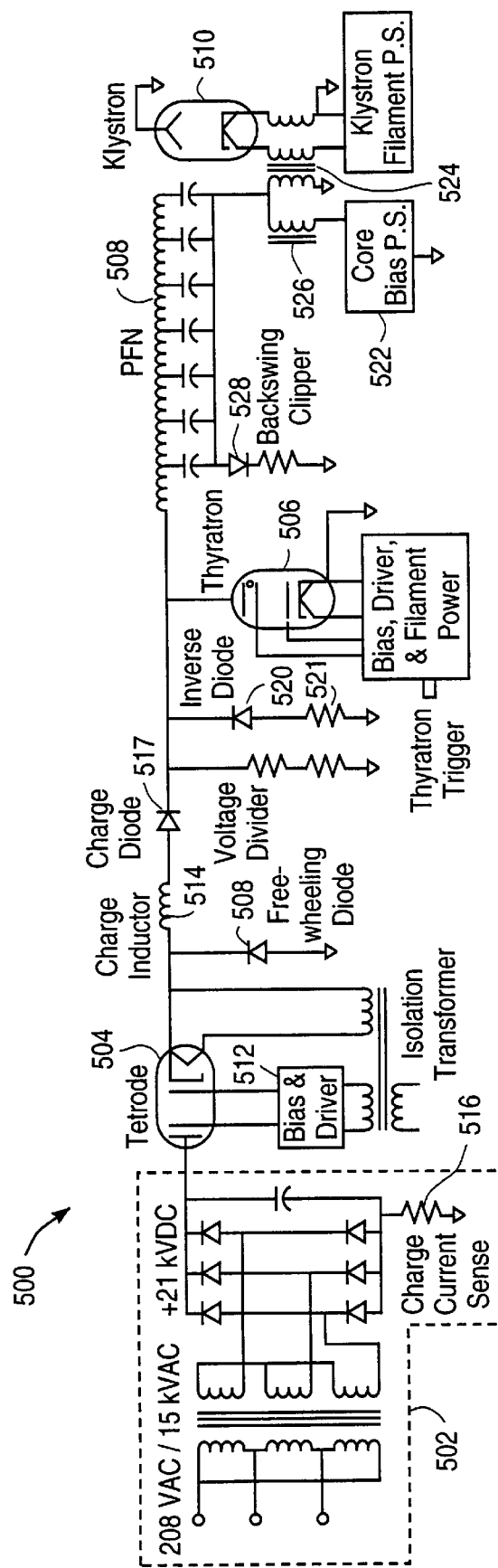
FIG. 3 is a schematic showing a command charge line type modulator.

The operation of pulse transformer 634 and klystron 620 is substantially the same as for the modulators of FIGS. 3 and 4. There is one major exception, however. According to this embodiment of the invention, the PFN impedance is designed to be slightly less than the impedance of the load. This causes the reflected voltage from PFN 616 to be positive, rather than negative as described above with reference to FIGS. 3 and 4. This is done because SCR switch assembly 612 does not require an inverse voltage to switch off, obviating the need for the HV, high power inverse diode assembly 520 and resistor 521 of FIGS. 3 and 4.

While the invention has been particularly shown and described with reference to specific embodiments thereof, it will be understood by those skilled in the art that changes in the form and details of the disclosed embodiments may be made without departing from the spirit or scope of the invention. Therefore, the scope of the invention should be determined with reference to the appended claims.

What is claimed is:

1. A line type modulator for modulating an RF power device in a medical linear accelerator, comprising:
   a low voltage DC power source;
   a flyback transformer having a primary winding and a secondary winding;
   current sensing circuitry for sensing current in the primary winding of the flyback transformer and generating a current sense signal indicative thereof;
   a switching stage coupled between the DC power source and the flyback transformer, the switching stage comprising at least one solid-state device for electrically connecting and disconnecting the DC power source and the primary winding of the flyback transformer in response to a control signal;
   control circuitry coupled to the current sensing circuitry and the switching stage for generating the control signal in response to the current sense signal;
   a charge diode assembly, the anode of which is coupled to the secondary winding of the flyback transformer;
   a delay element coupled to the cathode of the charge diode assembly;
   a pulse forming network coupled to the delay element for generating an energy pulse;
   a solid-state switch assembly coupled to the cathode of the charge diode assembly for discharging energy stored in the pulse forming network via the delay element in response to a trigger signal; and
   a first pulse transformer for delivering the energy pulse to the RF power device, the first pulse transformer having a primary winding coupled to the pulse forming network and a secondary winding for coupling to the RF power device.

2. The line type modulator of claim 1 wherein the low voltage DC power supply comprises a 3-phase bridge rectifier coupled to a capacitor.

3. The line type modulator of claim 1 wherein the primary and secondary windings of the flyback transformer are oppositely wound.

4. The line type modulator of claim 1 wherein the current sensing circuitry comprises a DC current transformer.

5. The line type modulator of claim 1 wherein the delay element comprises a saturable delay reactor.

6. The line type modulator of claim 1 where the impedance of the pulse forming network is less than the impedance of the RF power device.

7. The line type transformer of claim 1 further comprising at least one freewheeling diode for providing a current path from the primary winding of the flyback transformer to the DC power source when the switching stage disconnects the DC power source and the primary winding of the flyback transformer.

8. The line type modulator of claim 1 wherein the pulse forming network comprises a network of capacitors and inductors, selected ones of the inductors having tuning slugs associated therewith, each of which is operable to vary the inductance of the associated inductor and thereby modify a waveform associated with the energy pulse.

9. The line type modulator of claim 8 wherein the tuning slugs are aluminum.

10. The line type modulator of claim 1 wherein the at least one solid-state device of the switching stage comprises first and second insulated gated bipolar transistors (IGBTs).

11. The line type modulator of claim 9 wherein the collector of the first IGBT is coupled to a positive terminal of the DC power source and the emitter of the first IGBT is coupled to a first side of the primary winding of the flyback transformer, and wherein the collector of the second IGBT is coupled to a second side of the primary winding of the flyback transformer and the emitter of the second IGBT is coupled to a negative terminal of the DC power source.

12. The line type modulator of claim 9 further comprising IGBT gate driver circuitry coupled to the gates of the first and second IGBTs and the control circuitry for providing drive signals to the first and second IGBTs in response to the control signal.

13. The line type modulator of claim 11 wherein the IGBT gate driver circuitry is optically coupled to the control circuitry.

14. The line type modulator of claim 1 wherein the solid-state switch assembly comprises a plurality of silicon controlled rectifiers (SCRs).

15. The line type modulator of claim 14 further comprising a voltage divider network coupled to the plurality of SCRs to ensure that potentials across the SCRs are substantially the same.

16. The line type modulator of claim 14 further comprising a plurality of zener diodes, each of which is coupled to an SCR to ensure that trigger voltages applied to the SCRs are substantially the same.

17. The line type modulator of claim 14 further comprising trigger circuitry coupled to the plurality of SCRs for transmitting the trigger signal substantially simultaneously to each of the SCRs.

18. The line type modulator of claim 17 wherein the trigger circuitry comprises a second pulse transformer having a primary winding and a plurality of secondary windings, each of the secondary windings being associated with one of the SCRs.

19. A medical linear accelerator, comprising:
   an RF power device for generating high power RF pulses;
   a line-type modulator coupled to the RF power device for modulating the RF power device, the line type modulator comprising:
      a low voltage DC power source;
      a flyback transformer having a primary winding and a secondary winding;
      current sensing circuitry for sensing current in the primary winding of the flyback transformer and generating a current sense signal indicative thereof;
      a switching stage coupled between the DC power source and the flyback transformer, the switching stage comprising at least one solid-state device for electrically connecting and disconnecting the DC power source and the primary winding of the flyback transformer in response to a control signal;
      control circuitry coupled to the current sensing circuitry and the switching stage for generating the control signal in response to the current sense signal;
      a charge diode assembly, the anode of which is coupled to the secondary winding of the flyback transformer;
      a delay element coupled to the cathode of the charge diode assembly;
      a pulse forming network coupled to the delay element for generating an energy pulse;
      a solid-state switch assembly coupled to the cathode of the charge diode assembly for discharging energy stored in the pulse forming network via the delay element in response to a trigger signal;
      a pulse transformer for delivering the energy pulse to the RF power device, the pulse transformer having a primary winding coupled to the pulse forming network and a secondary winding coupled to the RF power device;

a source of electrons;

an accelerator tube coupled to the RF power device and the source of electrons for generating a beam of high energy electrons; and a treatment head for receiving the beam of high energy electrons.

20. The medical linear accelerator of claim 19 wherein the RF power device comprises a klystron.

21. The medical linear accelerator of claim 19 wherein the RF power device comprises a magnetron.

* * * * *